United States Patent [19]

Igari et al.

[11] Patent Number: 5,665,394
[45] Date of Patent: Sep. 9, 1997

[54] MATRIX FOR SUSTAINED-RELEASE PREPARATION

[75] Inventors: Yasutaka Igari, Hyogo; Akira Saikawa; Kayoko Okamoto, both of Osaka; Shigeru Kamei, Hyogo; Masahisa Oka, Kanagawa; Atsunori Sano, Saitama, all of Japan

[73] Assignees: Takeda Chemical Industries, Ltd.; Wako Purechemical Industries, Ltd., both of Osaka, Japan

[21] Appl. No.: 723,152

[22] Filed: Sep. 30, 1996

Related U.S. Application Data

[62] Division of Ser. No. 391,699, Feb. 21, 1995, Pat. No. 5,594,091.

[30] Foreign Application Priority Data

Feb. 21, 1994 [JP] Japan .................................. 6-022858
Feb. 21, 1994 [JP] Japan .................................. 6-022880

[51] Int. Cl.$^6$ ........................... A61K 9/50; A61K 9/48; A61F 2/02; A61F 9/02
[52] U.S. Cl. ...................... 424/501; 424/426; 424/434; 424/436; 424/451; 424/464; 514/772.3; 514/785
[58] Field of Search ..................... 424/426, 434, 424/436, 451, 464, 501; 514/772.3, 785

[56] References Cited

U.S. PATENT DOCUMENTS

| | | | |
|---|---|---|---|
| 3,853,837 | 12/1974 | Fujino et al. | 260/112.5 |
| 3,972,859 | 8/1976 | Fujino et al. | 260/112.5 LH |
| 4,008,209 | 2/1977 | Fujino et al. | 260/112.5 LH |
| 4,086,219 | 4/1978 | Wittle et al. | 260/112.5 LH |
| 4,087,390 | 5/1978 | Shields | 260/8 |
| 4,093,574 | 6/1978 | Shields | 260/8 |
| 4,100,117 | 7/1978 | Shields | 260/8 |
| 4,124,577 | 11/1978 | Tinney et al. | 260/112.5 LH |
| 4,229,438 | 10/1980 | Fujino et al. | 424/177 |
| 4,229,997 | 10/1980 | Sarantakis | 260/8 |
| 4,253,998 | 3/1981 | Sarantakis | 260/8 |
| 4,277,394 | 7/1981 | Fujino et al. | 260/8 |
| 4,317,815 | 3/1982 | Coy et al. | 424/177 |
| 4,801,739 | 1/1989 | Franz et al. | |
| 5,110,904 | 5/1992 | Haviv et al. | 530/313 |
| 5,302,694 | 4/1994 | Buchholz | 528/354 |
| 5,319,038 | 6/1994 | Tunc | 525/415 |

FOREIGN PATENT DOCUMENTS

| | | |
|---|---|---|
| 0 145 240 | 6/1985 | European Pat. Off. . |
| 0 481 732 | 4/1992 | European Pat. Off. . |
| 2 537 980 | 6/1984 | France . |
| 62-212423 | 9/1987 | Japan . |
| 63-92641 | 4/1988 | Japan . |
| 2-212436 | 8/1990 | Japan . |
| 4-173746 | 6/1992 | Japan . |
| 672 133 | 10/1989 | Switzerland . |
| 2 145 422 | 3/1985 | United Kingdom . |

*Primary Examiner*—Carlos A. Azpuru
*Attorney, Agent, or Firm*—Foley & Lardner

[57] ABSTRACT

The present invention relates to a matrix for sustained-release preparation comprising an ester formed at a terminal carboxyl group of a straight-chain polyester which essentially consists of an α-hydroxymonocarboxylic acid. The matrix is stable to light, heat, moisture, coloring etc., and is of low toxicity. The sustained-release preparation produced by using the ester of the present invention offers stable drug release over an extended period of time, ensuring sustained stable effect. Furthermore, the sustained-release preparation does not show excess drug release just after administration.

10 Claims, No Drawings

MATRIX FOR SUSTAINED-RELEASE PREPARATION

This application is a divisional of application Ser. No. 08/391,699, filed Feb. 21, 1995 now U.S. Pat. No. 5,594,091.

BACKGROUND OF THE INVENTION

The present invention relates to a matrix for sustained-release preparation and a sustained-release preparation comprising it.

EP-A 481732 (Japanese Patent Unexamined Publication No. 112468/1993) describes a base for sustained-release preparation comprising a mixture of polylactic acid and a glycolic acid/hydroxycarboxylic acid [$HOCH(C_{2-8}$ alkyl)$COOH$] copolymer.

Japanese Patent Unexamined Publication No. 212436/1990 describes a base for sustained-release preparation obtained by direct dehydrative poly-condensation process of lactic acid and/or glycolic acid and an oxycarboxylic acid.

Japanese Patent Unexamined Publication No. 173746/1992 describes a sustained-release drug-polymer complex prepared by adding a drug to a polymer mixture of a lactic acid/glycolic acid copolymer and poly-$\gamma$-butyrolactone, poly-$\delta$-valerolactone and/or poly-$\epsilon$-caprolactone.

Japanese Patent Unexamined Publication No. 212423/1987 describes polymers or copolymers of esters of hydroxypoly carboxylic acids such as an ethyl ester of polymalic acid.

Japanese Patent Unexamined Publication No. 92641/1988 describes $\beta$-benzylmalate.lactic acid copolymer.

However, these are different in structure from the ester formed at a terminal carboxyl group of a straight-chain polyester which essentially consists of an $\alpha$-hydroxymonocarboxylic acid.

In sustained-release preparations wherein a drug is dispersed in a biodegradable polymer, it is desirable that drug release be controlled freely. In general, drug release duration for a sustained-release preparation depends on the composition and molecular weight of the base biodegradable polymer. Initial drug release following administration of the sustained-release preparation is sometimes excessive, which can result in a rapidly increased local drug concentration, and hence a rapidly increased blood level, leading to undesirable action. There is therefore need to develop a matrix for sustained-release preparation enabling production of a sustained-release preparation of low initial drug release.

According to the present invention, there is provided:

(1) A matrix for sustained-release preparation comprising an ester formed at a terminal carboxyl group of a straight-chain polyester which essentially consists of an $\alpha$-hydroxymonocarboxylic acid, the polyester having a weight-average molecular weight of about 1,500 to about 50,000, (2) The matrix according to term (1) above, wherein the straight-chain polyester if a lactic acid/glycolic acid copolymer, (3) The matrix according to term (1) above, wherein the ester is an alkyl ester, (4) The matrix according to term (3) above, wherein the alkyl ester is a $C_{1-3}$ alkyl ester, (5) A sustained-release preparation which comprises the matrix as defined in term (1) above and a biologically active peptide, (6) The sustained-release preparation according to term (5) above, wherein the biologically active peptide is an LH-RH analogue, (7) The sustained-release preparation according to term (6) above, wherein the LH-RH analogue is an LH-RH antagonist, (8) The sustained-release preparation according to term (5) above, wherein the biologically active peptide is a cytokine, (9) The sustained-release preparation according to term (8) above, wherein the cytokine is an interferon,

(10) An injectable preparation which comprises the sustained-release preparation as defined in term (5) above,

(11) An ester formed at a terminal carboxyl group of a straight-chain polyester which essentially consists of an $\alpha$-hydroxymonocarboxylic acid, the polyester having a weight-average molecular weight of about 1,500 to about 50,000

(12) The ester according to term (11) above, which is an ester formed at a terminal carboxyl group of a lactic acid/glycolic acid copolymer,

(13) The ester according to term (11) above, which is an alkyl ester, and

(14) The ester according to term (13) above, which is a $C_{1-3}$ alkyl ester.

DETAILED DESCRIPTION OF THE INVENTION

In the present specification, weight-average molecular weight and number-average molecular weight are those in terms of polystyrene as determined by gel permeation chromatography (GPC). Measurements were taken using a GPC column KF804L×2 (produced by Showa Denko) with chloroform as a mobile phase.

The dispersity is calculated by the formula: (weight-average molecular weight/number-average molecular weight).

In the present invention, the straight-chain polyester having a terminal carboxyl group essentially consists of an $\alpha$-hydroxymonocarboxylic acid, has the weight-average molecular weight of about 1,500 to about 50,000 is sparingly soluble or insoluble in water, is biocompatible, and is biodegradable.

A straight-chain polyester having a terminal carboxyl is a straight-chain polyester in which the number-average molecular weight by GPC determination is almost the same as that by end-group determination.

The number-average molecular weight is calculated as follows:

First, the polyester (about 1 to 3 g) is dissolved in a mixed solvent of acetone (25 ml) and methanol (5 ml); the solution is quickly titrated with a 0.05N alcoholic solution of potassium hydroxide while stirring at room temperature (20° C.) with phenolphthalein as an indicator to determine the carboxyl group content; the number-average molecular weight by end-group determination is calculated from the following equation:

Number-average molecular weight by end-group determination=20,000×A/B where A is the weight mass (g) of the polyester, and B is the amount (ml) of the 0.05N alcoholic potassium hydroxide solution added until the titration end point is reached.

This value is hereinafter referred to as the number-average molecular weight by end-group determination.

For example, in the case of a polymer having a terminal carboxyl group as synthesized from one or more $\alpha$-hydroxymonocarboxylic acids by catalyst-free dehydrative poly-condensation process, the number-average molecular weights by GPC determination and end-group determination almost agree with each other. On the other hand, in the case of a polyester having substantially no free-terminal carboxyl group as synthesized from a cyclic dimer by ring-opening polymerization process using a catalyst, the number-average molecular weight by end-group determination is significantly higher than that by GPC determination. This difference makes it possible to clearly differentiate a polyester having a terminal carboxyl group from a polyester having substantially no terminal carboxyl group.

While the number-average molecular weight by end-group determination is an absolute value, that by GPC determination is a relative value that varies depending on various analytical conditions (e.g., kind of mobile phase, kind of column, reference substance, slice width, baseline); it is therefore difficult to have an absolute numerical representation of both values. However, the fact that the number-average molecular weights by GPC determination and end-group determination almost agree with each other means that the number-average molecular weight by end-group determination falls within the range from about 0.4 to 2 times, preferably from about 0.5 to 2 times, and more preferably from about 0.8 to 1.5 times, that by GPC determination. Also, the fact that the number-average molecular weight by end-group determination is significantly higher than that by GPC determination means that the number-average molecular weight by end-group determination is over about 2 times that by GPC determination.

The weight-average molecular weight of the straight-chain polyester of the present invention which essentially consists of an α-hydroxymonocarboxylic acid (hereinafter also referred to as straight-chain polyester having a terminal carboxyl group) is about 1,500 to 50,000. The weight-average molecular weight is preferably about 2,000 to 40,000, more preferably about 5,000 to 25,000.

Reference to an α-hydroxymonocarboxylic acid includes both a single α-hydroxymonocarboxylic acid or mixtures of several α-hydroxymonocarboxylic acids.

Examples of the straight-chain polyester having a terminal carboxyl group is an α-hydroxymonocarboxylic acid(s) (e.g., glycolic acid, lactic acid, 2-hydroxybutyric acid, 2-hydroxyvaleric acid, 2-hydroxy-3-methylbutyric acid, 2-hydroxycaproic acid, 2-hydroxyisocaproic acid, 2-hydroxycaprylic acid) in the form of a homopolymer (e.g., lactic acid polymer), a copolymer (e.g. lactic acid/glycolic acid copolymer, 2-hydroxybutyric acid/glycolic acid copolymer) or a mixture of these homopolymers and/or copolymers (e.g. mixture of lactic acid polymer and 2-hydroxybutyric acid/glycolic acid copolymer).

Particularly preferable straight-chain polyesters having a terminal carboxyl group include the lactic acid/glycolic acid copolymer described in Japanese Patent Unexamined Publication No. 28521/1986 and the mixture of (A) polylactic acid and (B) glycolic acid/α-hydroxycarboxylic acid [HOCH(C$_{2-8}$ alkyl)COOH] coplymer described in Japanese Patent Unexamined Publication No. 112468/1993.

For example, when a lactic acid/glycolic acid copolymer is used, the content ratio (mol %) of lactic acid/glycolic acid is preferably 100/0 to about 40/60, more preferably about 90/10 to 50/50. Here, lactic acid/glycolic acid which has the content ratio of 100/0 means a homopolymer of lactic acid.

The weight-average molecular weight of the lactic acid/glycolic acid copolymer is preferably about 5,000 to 25,000, more preferably about 7,000 to 20,000. The dispersity of the lactic acid/glycolic acid copolymer (weight-average molecular weight/number-average molecular weight) is preferably about 1.2 to 4.0, more preferably about 1.5 to 3.5.

The decomposition/elimination rate of a lactic acid/glycolic acid copolymer varies widely, depending on composition or molecular weight. However, a drug release duration can be extended by lowering the glycolic acid ratio or increasing the molecular weight, since decomposition/elimination is delayed as the glycolic acid ratio decreases. Conversely, drug release duration can be shortened by increasing the glycolic acid ratio or decreasing the molecular weight.

For example, when a mixture of (A) polylactic acid and (B) glycolic acid/α-hydroxycarboxylic acid [HOCH(C$_{2-8}$ alkyl)COOH] copolymer is used, the hydroxycarboxylic acid is preferably 2-hydroxybutyric acid, 2-hydroxyvaleric acid, 2-hydroxy-3-methylbutyric acid, 2-hydroxycaproic acid, or the like, with greater preference given to 2-hydroxybutyric acid. Although the hydroxycarboxylic acid may be of the D-, L- or D,L-configuration, it is preferably to use a mixture of the D- and L-configurations. In such case, the ratio of the D-/L-configuration (mol %) preferably falls within the range from about 75/25 to 25/75, more preferably from about 60/40 to 40/60, and still more preferably from about 55/45 to 45/55.

With respect to the glycolic acid/α-hydroxycarboxylic acid [HOCH(C$_{2-8}$ alkyl)COOH] copolymer (hereinafter glycolic acid copolymer), it is preferable that the content ratio of glycolic acid to hydroxycarboxylic acid is about 10 to 75 mol %, more preferably about 20 to 75 mol %. The weight-average molecular weight of the above-described glycolic acid copolymer is normally about 2,000 to 50,000, preferably about 3,000 to 40,000, and more preferably about 8,000 to 40,000. The dispersity of the glycolic acid copolymer (weight-average molecular weight/number-average molecular weight) is preferably about 1.2 to 4.0, more preferably about 1.5 to 3.5.

Although the above-described polylactic acid may be of the D- or L-configuration or a mixture thereof, it is preferable to use a mixture of the D- and L-configurations. The ratio of the D-/L-configuration (mol %) preferably falls within the range from about 75/25 to 20/80, more preferably from about 60/40 to 25/75, and still more preferably from about 55/45 to 25/75. The weight-average molecular weight of the polylactic acid is preferably about 1,500 to 30,000, more preferably about 2,000 to 20,000, and still more preferably about 3,000 to 15,000. The dispersity of the polylactic acid (weight-average molecular weight/number-average molecular weight) is preferably about 1.2 to 4.0, more preferably about 1.5 to 3.5.

The mixing ratio of (A) polylactic acid and (B) glycolic acid copolymer [(A)/(B) (weight %)] is normally about 10/90 to 90/10, preferably about 20/80 to 80/20, and more preferably about 30/70 to 70/30. If component (A) or (B) is in excess, the preparation obtained shows nothing more than almost the same drug release pattern as obtained with component (A) or (B) alone; zero order release pattern owing to the mixed matrix is not obtained in the latter phase of drug release. The decomposition/elimination rates of glycolic acid copolymer and polylactic acid vary widely, depending on composition or molecular weight. However, drug release duration can be extended by increasing the molecular weight of the polylactic acid or the mixing ratio (A)/(B), since the decomposition/elimination rate of glycolic acid copolymer is usually higher than that of polylactic acid. Conversely, drug release duration can be shortened by decreasing the molecular weight of polylactic acid or mixing ratio (A)/(B). Drug release duration can also be adjusted by altering the kind and content ratio of hydroxycarboxylic acid used.

The ester formed at the terminal carboxyl group is exemplified by pharmacologically acceptable esters and include alkyl esters, aryl esters, aralkyl esters.

Here, alkyl esters are exemplified by esters of alkyl groups having 1 to 6 carbon atoms, such as methyl, ethyl, n-propyl, isopropyl, n-butyl, isobutyl, sec-butyl, tert-butyl, n-pentyl, isopentyl, sec-pentyl, neo-pentyl, tert-pentyl, 1-ethylpropyl, n-hexyl, isohexyl, 1,1-dimethylbutyl, 2,2-dimethylbutyl, 3,3-dimethylbutyl and 2-ethylbutyl, which alkyl groups may have 1 to 3 substituents selected from halogen atoms such as chlorine, bromine and fluorine, $(C_{1-8})$alkyl-carbonyl groups such as methylcarbonyl, ethylcarbonyl and butylcarbonyl, and the nitro group.

Examples of aryl esters include esters of aryl groups having 6 to 10 carbon atoms, such as phenyl and naphthyl, which aryl groups may have 1 to 3 substituents selected from halogen atoms such as chlorine, bromine and fluorine, $(C_{1-6})$alkyl-carbonyl groups such as methylcarbonyl, ethylcarbonyl and butylcarbonyl, and the nitro group.

Examples of aralkyl esters include esters of aralkyl groups having 7 to 19 carbon atoms, such as benzyl, phenylethyl, naphthylmethyl and trityl, which aralkyl groups may have 1 to 3 substituents selected from halogen atoms such as chlorine, bromine and fluorine, $(C_{1-6})$alkyl-carbonyl groups such as methylcarbonyl, ethylcarbonyl and butylcarbonyl, and the nitro group.

The ester formed at the terminal carboxyl group is preferably an alkyl ester. More preferable esters are esters of alkyl groups having 1 to 6 carbon atoms, such as methyl, ethyl, n-propyl, isopropyl, n-butyl, isobutyl, sec-butyl, tert-butyl, n-pentyl, isopentyl, sec-pentyl, neo-pentyl, tert-pentyl, 1-ethylpropyl, n-hexyl, isohexyl, 1,1-dimethylbutyl, 2,2-dimethylbutyl, 3,3-dimethylbutyl and 2-ethylbutyl, which alkyl groups may have 1 to 3 substituents selected from $(C_{1-6})$alkyl-carbonyl groups such as methylcarbonyl, ethylcarbonyl and butylcarbonyl, and the nitro group.

Particularly preferable esters include esters of alkyl groups having 1 to 3 carbon atoms, such as methyl, ethyl, n-propyl and isopropyl.

The ester of the present invention is produced by esterifying the terminal carboxyl group of a straight-chain polyester which essentially consists of an α-hydroxymonocarboxylic acid and has the weight-average molecular weight of about 1,500 to about 50,000 (hereinafter also referred to as starting polymer). This esterification is carried out by per se known methods as follows:

(1) The starting polymer is reacted in a mixture of a diazolakane (e.g., diazomethane, phenyldiazomethane, diphenyldiazomethane) and a solvent that does not interfere with the reaction (e.g., ether such as tetrahydrofuran or dioxane, ester such as ethyl acetate, nitrile such as acetonitrile, halogenated hydrocarbon such as dichloromethane or dichloroethane). Reaction temperature is about 0° C. to refluxing temperature. Reaction time is about 2 minutes to 20 hours.

(2) An alkali metal salt (e.g., sodium salt, potassium salt, lithium salt) of the starting polymer is reacted with an activated alkyl halide (e.g., methyl iodide, benzyl bromide, n-nitro-benzyl bromide, m-phenoxybenzyl bromide, p-t-butylbenzyl bromide, pivaloyloxymethyl chloride). This reaction is carried out in a solvent that does not interfere with the reaction (e.g., amide such as dimethylformamide, dimethylacetamide or hexamethylphosphoramide, ketone such as acetone). Reaction temperature is about 0° to 60° C. Reaction time is about 2 minutes to 4 hours. The reaction is not hampered even in the presence of triethylamine etc. in the reaction mixture.

(3) The starting polymer is reacted with an alcohol, such as methanol, ethanol or benzyl alcohol. This reaction is carried out in the presence of a carbodiimide as a condensing agent (e.g., dicyclohexylcarbodiimide, 1-ethyl-3-(3-dimethylaminoisopropyl)-carbodiimide. Reaction temperature is about 0° C. to refluxing temperature. Reaction time is about 15 minutes to 18 hours. Solvents that do not interfere with the reaction are used, including halogenated hydrocarbons, such as chloroform, dichloromethane and dichloroethane.

(4) The starting polymer is reacted with an acid halide (e.g., ethyl chloroformate, benzyl chloroformate); the resulting acid anhydride is reacted with an alcohol (e.g., methanol, ethanol, benzyl alcohol) under the conditions described in term (3) above. This acid anhydride is obtained by reacting the starting polymer with an acid halide, such as an acid chloride, in a solvent that does not interfere with the reaction (e.g., ether such as tetrahydrofuran, halogenated hydrocarbon such as dichloromethane). Reaction temperature is about 25° C. to refluxing temperature. Reaction time is about 15 minutes to 10 hours.

The ester of the present invention is used as a matrix for sustained-release preparations, such as microcapsules.

With respect to the ester of the present invention, there is almost no hydrogen bond between carboxyl groups and almost no reaction between basic drug and terminal carboxyl group. Therefore, in a sustained-release preparation produced by using this ester, initial drug release immediately following administration is suppressed, by delay of water permeation into the preparation and other reasons, due to increased base hydrophobicity. And further, the matrix for sustained-release preparation comprising the ester of the present invention is advantageously used as a matrix for sustained-release preparation capable of releasing a drug over an extended period of time, because the matrix is rather slow in the rate of hydrolysis than a matrix for sustained-release preparation consisting of a straight-chain polyester having a terminal carboxyl group.

It is preferably that, as a matrix for sustained-release preparation, the ester of the present invention be used in combination with a straight-chain polyester having a terminal carboxyl group. Here, the straight-chain polyester having a terminal carboxyl group is identical with that described above. The mixing ratio by weight if normally about 100/0 to 5/95, preferably about 100/0 to 30/70, and more preferably about 100/0 to 50/50.

Both the ester of the present invention (C) and the straight-chain polyester having a terminal carboxyl group (D), and used in combination therewith, may be a copolymer or homopolymer. Also, 3 or more straight-chain polyesters, e.g., 1 kind of (C) and 2 kinds of (D), may be used in combination. The kind, weight-average molecular weight, dispersion value and other factors of the straight-chain polyester having a terminal carboxyl group, and the kind, weight-average molecular weight and other factors of the ester of the present invention, are chosen to obtain the desired drug release duration and to satisfactorily suppress excess initial drug release following administration.

A typical example of such combination is the combination of a lactic acid/glycolic acid copolymer having an alkyl-esterified terminal carboxyl group (E) and a lactic acid/glycolic acid copolymer having a terminal carboxyl group (F). The ratio of weight of (E) and (F) is normally about 100/0 to 5/95, preferably about 100/0 to 20/80, and more preferably about 100/0 to 50/50. Components (E) and (F) may or may not have the same lactic acid/glycolic acid ratio, and may or may not have the same weight-average molecular weight.

Another typical example is the combination of a polylactic acid having an alkyl-esterified terminal carboxyl group (G) and a glycolic acid/2-hydroxybutyric acid copolymer having a terminal carboxyl group (H). The ratio by weight of (G) and (E) is normally about 100/0 to 5/95, preferably about 100/0 to 20/80, and more preferably from about 100/0 to 50/50. Components (G) and (H) may or may not have the same weight-average molecular weight.

The matrix for sustained-release preparation comprising the ester of the present invention is prepared as a sustained-release preparation using a given drug.

Useful drugs include, but are not limited to, biologically active peptides, antitumor agents, antibiotics, antipyretic analgesic anti-inflammatory agents, antitussive expectorants, sedatives, muscle relaxants, antiepileptics, antiulcer agents, antidepressants, anti-allergic agents, cardiotonics, antiarrhythmic agents, vasodilators, hypotensive diuretics, antidiabetics, anticoagulants, hemostatics, antituberculosis drugs, hormones, narcotic antagonists, osteoporosis remedies and angiogenesis inhibitors.

Biologically active peptides consisting of 2 or more amino acids and having a molecular weight of about 200 to 80,000 are preferred.

Examples of biologically active peptides include luteinizing hormone-releasing hormone (LH-RH) and similarly acting analogs, such as the peptide represented by the following formula [I]:

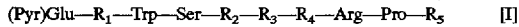

(Pyr)Glu—R$_1$—Trp—Ser—R$_2$—R$_3$—R$_4$—Arg—Pro—R$_5$   [I]

wherein R$_1$ represents His, Tyr, Trp or p—NH$_2$—Phe; R$_2$ represents Tyr or Phe; R$_3$ represents Gly or a D-type amino acid residue; R$_4$ represents Leu, Ile or Nle; R$_5$ represents Gly—NH—R$_6$ (R$_6$ is H or a lower alkyl group with or without a hydroxyl group) or NH—R$_6$ (R$_6$ has the same definition as defined above), or a salt thereof [see U.S. Pat. Nos. 3,853,837, 4,008,209 and 3,972,859, British Patent No. 1,423,083, Proceedings of the National Academy of Science of the United States of America, Vol. 78, pp. 6509–6512 (1981)].

With respect to formula [I] above, the D-type amino acid residue for R$_3$ is exemplified by α-D-amino acids having up to 9 carbon atoms (e.g., D-Leu, Ile, Nle, Val, Nval, Abu, Phe, Phg, Ser, Thr, Met, Ala, Trp, α-Aibu). These amino acid residues may have a protecting group (e.g., t-butyl, t-butoxy, t-butoxycarbonyl) as appropriate. Acid salts (e.g., carbonate, bicarbonate, acetate, propionate) and metal complex compounds (e.g., copper complex, zinc complex) of peptide [I] can also be used as is peptide [I].

Abbreviations for amino acids, protecting groups and others in the peptide represented by formula [I] and the following peptides are based on abbreviations specified by the IUPAC-IUB Commission of Biochemical Nomenclature or abbreviations in common use in relevant fields. When an optical isomer may be present in amino acid, it is of the L-configuration, unless otherwise stated.

A representative compound of formula [I] above is a peptide having His for R$_1$, Tyr for R$_2$, D-Leu for R$_3$, Leu for R$_4$ and NHCH$_2$—CH$_3$ for R$_5$ (acetate of this peptide, commonly termed leuprorelin acetate, is hereinafter also referred to as TAP-144).

LH-RH analogs include LH-RH antagonists (see U.S. Pat. Nos. 4,086,219, 4,124,577, 4,253,997 and 4,137,815).

Examples of biologically active peptides include cytokines, such as lymphokines and monokines. Examples of lymphokines include interferons (alpha, beta, gamma) and interleukins (IL-2 through IL-12). Examples of monokines include interleukin (IL-1), and tumor necrosis factor (TNF). Preferable cytokines are lymphokines, with greater preference given to interferons (alpha, beta, gamma).

Examples of biologically active peptides include insulin, somatostatin, somatostatin derivatives (see U.S. Pat. Nos. 4,087,390, 4,093,574, 4,100,117 and 4,253,998), growth hormones, prolactin, adrenocorticotropic hormone (ACTH), melanocyte-stimulating hormone (MSH), thyroid hormone-releasing hormone [represented by the structural formula Pyr(Glu-His-ProNH$_2$, hereinafter also referred to as TRH] and salts and derivatives thereof (see Japanese Patent Unexamined Publication Nos. 121273/1975 and 116465/1977), thyroid-stimulating hormone (TSH), luteinizing hormone (LH), follicle-stimulating hormone (FSH), vasopressin, vasopressin derivatives [desmopressin, see Folia Endocrinologica Japonica, Vol. 54, No. 5, pp. 676–691 (1978)], oxytocin, calcintonin, parathyroid hormone, glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Publication No. 31567), endorphin, kyotorphin, tuftsin, thymopoietin, thymosin, thymostimulin, thymic humoral factor (THF), blood thymic factor (FTS) and derivatives thereof (see U.S. Pat. No. 4,229,438), other thymic factors [Igaku no Ayumi, Vol. 125, No. 10, pp. 835–843 (1983)], colony-stimulating factor (CSF), motilin, daynorphin, bombesin, neurotensin, caerulein, bradykinin, urokinase, asparaginase, kallikrein, substance P, nerve growth factor, cell growth factor, nerve nutrition factor, blood coagulation factors VIII and IX, lysozyme chloride, polymixin B, colistin, gramicidin, bacitracin, erythropoietin (EPO), thrombopoietin, endothelin-antagonist peptides (see European Patent Publication Nos. 436189, 457195 and 496542, and Japanese Patent Unexamined Publication Nos. 94692/1991 and 130299/1991), fragments of these biologically active peptides and derivatives thereof.

Examples of antitumor agents include bleomycin, methotrexate, actinomycin D, mitomycin C, binblastin sulfate, bincrystin sulfate, daunorubicin, adriamycin, neocartinostatin, cytosinearabinoside, fluorouracil, tetrahydrofuryl-5-fluorouracil, krestin, Picibanil, lentinan, levamisole, Bestatin, adimexon, glycyrrhizin, polyI:C, polyA:U and polyICLC.

Examples of antibiotics include gentamicin, dibekacin, Kanendomycin, lividomycin, tobramycin, amikacin, fradiomycin, sisomycin, tetracycline hydrochloride, oxytetracycline hydrochloride, rolitetracycline, doxycycline hydrochloride, ampicillin, piperacillin, ticarcillin, cefalothin, cefaloridine, cefotiam, cefsulodin, cefmenoxime, cefmetazole, cefazolin, cefotaxime, cefoperazon, ceftizoxime, mochisalactam, thienamycin, sulfazecin and aztreonam.

Examples of antipyretic analgesic anti-inflammatory agents include salicylic acid, sulpyrine, flufenamic acid, diclofenac, indomethazin, morphine, pethidine hydrochloride, levorphanol tartrate and oxymorphone.

Examples of antitussive expectorants include ephedrine hydrochloride, methylephedrine hydrochloride, noscapine hydrochloride, codeine phosphate, dihydrocodeine phosphate, allocramide hydrochloride, clofedanol hydrochloride, picoperidamine hydrochloride, chloperastine, protokylol hydrochloride, isoproteranol hydrochloride, sulbutamol sulfate and tertbutaline sulfate.

Examples of sedatives include chloropromazine, prochlorperazine, trifluoroperazine, atropine sulfate and methylscopolamine bromide.

Examples of muscle relaxants include pridinol methanesulfonate, tubocurarine chloride and pancuronium bromide.

Examples of antiepileptics include phenytoin, ethosuximide, acetazolamide sodium and chlordiazepoxide.

Examples of antiulcer agents include metoclopramide and histidine hydrochloride.

Examples of antidepressants include imipramine, clomipramine, noxiptiline and phenerdine sulfate.

Examples of anti-allergic agents include diphenhydramine hydrochloride, chlorpheniramine maleate, tripelanamine hydrochloride, metodirazine hydrochloride, clemizole hydrochloride, diphenylpyraline hydrochloride and methoxyphenamine hydrochloride.

Examples of cardiotonics include trans-π-oxocamphor, theophyllol, aminophylline and etilefrine hydrochloride, Examples of antiarrhythmic agents include propranolol, alprenolol, bufetolol and oxprenolol.

Examples of vasodilators include oxyfedrine hydrochloride, diltiazem, tolazoline hydrochloride, hexobendine and bamethan sulfate.

Examples of hypotensive diuretics include hexamethonium bromide, pentolinium, mecamylamine hydrochloride, ecarazine hydrochloride and clonidine.

Examples of antidiabetics include glymidine sodium, glipizide, fenformin hydrochloride, buformin hydrochloride and metformin.

Examples of anticoagulants include heparin sodium and sodium citrate.

Examples of hemolytics include thromboplastin, thrombin, menadione sodium hydrogen sulfite, acetomenaphthone, ε-aminocaproic acid, tranexamic acid, carbazochrome sodium sulfonate and adrenochrome monoaminoguanidine methanesulfonate.

Examples of antituberculosis agents include isoniazid, ethambutol and p-aminosalicylic acid.

Examples of hormones include predonizolone, predonizolone sodium phosphate, dexamethasone sodium sulfate, betamethasone sodium phosphate, hexestrol phosphate, hexestrol acetate and methimazole.

Examples of narcotic antagonists include levallorphan tartrate, nalorphine hydrochloride and naloxone hydrochloride.

Examples of osteoporosis remedies include (sulfur-containing alkyl)aminomethylenebisphosphonic acid.

Examples of angiogenesis suppressors include angiogenesis-suppressing steroid [see Science, Vol. 221, p. 719 (1983)], fumagillin (see European Patent Publication No. 325119) and fumagillol derivatives (see European Patent Publication Nos. 357061, 359036, 386667 and 415294).

The above-described drugs may be used as such or as salts, preferably pharmacologically acceptable salts. Such salts include salts formed with inorganic acids (e.g., hydrochloric acid, sulfuric acid, nitric acid), organic acids (e.g., carbonic acid, succinic acid, acetic acid, propionic acid, trifluoroacetic acid) etc., when the drug has a basic group, such as the amino group. When the drug has an acidic group, such as the carboxyl group, such salts include salts formed with inorganic bases (e.g., alkali metals such as sodium and potassium, alkaline earth metals such as calcium and magnesium), organic bases (e.g., organic amines such as triethylamine and basic amino acids such as arginine) etc. The drug may form a metal complex compound (e.g., copper complex, zinc complex).

Since water-soluble drugs often show excess initial release, it is preferable to use a water-soluble drug for the present invention. The water solubility of a drug is defined as the n-octanol oil-water distribution ratio. It is preferable to use a drug whose oil-water distribution ratio is not higher than 1, preferably not higher than 0.1.

Oil-water distribution rates can be determined by the method described in "Butsuri Kagaku Jikkenho," by Jitsusaburo Samejima, published by Shokabo, 1961. Specifically, n-octanol and a buffer of pH 5.5 (1:1 by volume mixture) are placed in a test tube. The buffer is exemplified by Søerenzen buffer [Ergebnisse Der Physiology, 12, 393 (1912)], Clark-Lubs buffer [Journal of Bacteriology, 2, (1), 109, 191 (1917)], MacIlvaine buffer [Journal of Biological Chemistry, 49, 183, (1991)], Michaelis buffer [Die Wasserstoffionenkonzentration, p. 186 (1914)] and Kolthoff buffer [Biochemische Zeitschrift, 179, 410 (1926)]. An appropriate amount of such a drug is placed in the test tube, which is then stoppered and immersed in a constant-temperature chamber (25° C.) with occasional vigorous shaking. When the drug appears to have dissolved in both liquid phases to reach an equilibrium, the liquid mixture is kept standing or centrifuged; a given amount is pipetted from each of the upper and lower layers, and analyzed for drug concentration in each layer, to obtain the ratio of the drug concentration in the n-octanol layer to that in the water layer for the oil-water distribution rate.

Preferable drugs are biologically active peptides, more preferably LH-RH analogs or cytokines. Particularly preferable drugs include LH-RH antagonists and interferons (alpha, beta, gamma).

Examples of LH-RH antagonists include peptides and salts thereof, that are effective in treating hormone-dependent diseases, such as prostatic cancer, prostatic hypertrophy, endometriosis, uterine myoma, precocious puberty and breast cancer, and in contraception, including the peptides and salts thereof, that are described in U.S. Pat. No. 5,110,904, the Journal of Medicinal Chemistry, Vol. 34, pp. 2395–2402 (1991) and Recent Results in Cancer Research, Vol. 124, pp. 113–136 (1992).

More specifically, LH-RH antagonists are exemplified by the peptides represented by general formula [II]:

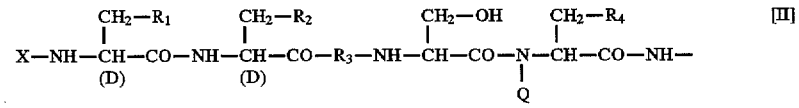

-continued

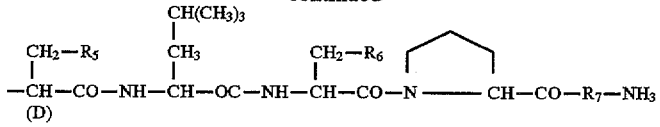

wherein X represents an acyl group; $R_1$, $R_2$ and $R_4$ independently represent an aromatic cyclic group; $R_3$ represents a D-amino acid residue or a group represented by the formula:

($R_3'$ represents a heterocyclic group); $R_5$ represents a group represented by the formula —$(CH_2)_n$—$R_5'$ (n is 2 or 3, $R_5'$ is an amino group which may be substituted), an aromatic cyclic group or an O-glycosyl group; $R_6$ represents a group represented by the formula —$(CH_2)_n$—$R_6'$ (n is 2 or 3, $R_6'$ is an amino group which may be substituted); $R_7$ represents a D-amino acid residue or an azaglycyl group; Q represents a hydrogen atom or a lower alkyl group, and salts thereof.

With respect to general formula [II], the acyl group for X is preferably one derived from a carboxylic acid. Said acyl group is exemplified by $C_{2-7}$ alkanoyl groups, $C_{7-15}$ cycloalkenoyl groups (e.g., cyclohexenoyl), $C_{1-6}$ alkylcarbamoyl groups (e.g., ethylcarbamoyl), 5- or 6-membered heterocyclic carbonyl groups (e.g., piperidinocarbonyl) and carbamoyl groups; these groups may be substituted.

The acyl group is preferably a $C_{2-7}$ alkanoyl group which may be substituted (e.g., acetyl, propionyl, butyryl, isobutyryl, pentanoyl, hexanoyl, heptanoyl), more preferably a $C_{2-4}$ alkanoyl group which may be substituted (e.g., acetyl, propionyl, butyryl, isobutyryl). Examples of substituents include $C_{1-6}$ alkylamino groups (e.g., methylamino, ethylamino, diethylamino, propylamino), $C_{1-3}$ alkanoylamino groups (e.g., formylamino, acetylamino, propionylamino), $C_{7-15}$ cycloalkenoylamino groups (e.g., cyclohexenoylamino), $C_{7-15}$ arylcarbonylamino groups (e.g., benzoylamino), 5- or 6-membered heterocyclic carboxamide groups (e.g., tetrahydrofurylcarboxamide, pyridylcarboxamide, furylcarboxamide), the hydroxyl group, carbamoyl group, formyl group, carboxyl group, and 5- or 6-membered heterocyclic groups (e.g., pyridyl, morpholino). Preferable substituents include 5- or 6-membered heterocyclic carboxamide groups (e.g., tetrahydrofurylcarboxamide, pyridylcarboxamide, furylcarboxamide).

X is preferably a $C_{2-7}$ alkanoyl group which may be substituted by a 5- or 6-membered heterocyclic carboxamide group, more preferably a $C_{2-4}$ alkanoyl group which may be substituted by a tetrahydrofurylcarboxamide group. Specifically, X is exemplified by acetyl and

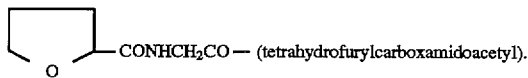

The tetrahydrofuryl group in the tetrahydrofurylcarboxamidoacetyl described above is preferably (2S)-tetrahydrofuryl group.

The aromatic cyclic group for $R_1$, $R_2$ or $R_4$ is exemplified by aromatic cyclic groups having 6 to 14 carbon atoms. Such groups include phenyl, naphthyl and anthryl, with preference given to aromatic cyclic groups having 6 to 10 carbon atoms, such as phenyl and naphthyl. These aromatic cyclic groups may have 1 to 5, preferably 1 to 3, appropriate substituents at appropriate positions thereon. Such substituents include the hydroxyl group, halogens, amino groups substituted by aminotriazolyl, and alkoxy groups, with preference given to the hydroxyl group, halogens, and amino groups substituted by aminotriazolyl.

Here, examples of halogens include fluorine, chlorine, bromine and iodine.

The aminotriazolyl group as a substituent for the amino group is exemplified by 3-amino-1H-1,2,4-triazol-5-yl, 5-amino-1H-1,3,4-triazol-2-yl, 5-amino-1H-1,2,4-triazol-3-yl, 3-amino-2H-1,2,4-triazol-5-yl, 4-amino-1H-1,2,3-triazol-5-yl and 4-amino-2H-1,2,3-triazol-5-yl.

The alkoxy group is preferably an alkoxy group having 1 to 6 carbon atoms (e.g., methoxy, ethoxy, propoxy, isopropoxy, butoxy, isobutoxy).

More preferably, $R_1$ is a naphthyl group or halogenophenyl group. $R_2$ is more preferably a halogenophenyl. $R_4$ is more preferably a hydroxyphenyl group or a phenyl group substituted by aminotriazolylamino.

The D-amino acid residue for $R_3$ is preferably an α-D-amino acid residue having 3 to 12 carbon atoms. Such amino acids include leucine, isoleucine, norleucine, valine, norvaline, 2-aminobutyric acid, phenylalanine, serline, threonine, methionine, alanine, tryptophan and aminoisobutyric acid. These amino acids hay have protecting groups (e.g., those in common use in relevant technical fields, such as t-butyl, t-butoxy, t-butoxycarbonyl) as appropriate.

The heterocyclic group for $R_3'$ is a 5- or 6-membered heterocyclic group which contains 1 or 2 hetero atoms of nitrogen or sulfur and which may be condensed with a benzene ring. Such heterocyclic groups include thienyl, pyrrolyl, thiazolyl, isothiazolyl, imidazolyl, pyrazolyl, pyridyl, 3-pyridyl, pyridazinyl, pyrimidinyl, pyrazinyl, 3-benzo[b]thienyl, 3-benzo[b]-3-thienyl, indolyl, 2-indolyl, isoindolyl, 1H-indazolyl, benzimidazolyl, benzothiazolyl, quinolyl and isoquinolyl. It is particularly preferable that $R_3'$ be pyridyl or 3-benzo[b]thienyl.

The aromatic cyclic group for $R_5$ is identical with that defined for $R_1$, $R_2$ or $R_4$ above. This aromatic cyclic group may have 1 to 5, preferably 1 to 3, appropriate substituents at appropriate positions thereon. Such substituents are identical with those defined for $R_1$, $R_2$ or $R_4$ above. Amino groups substituted by aminotriazolyl are preferred.

The glycosyl group in the O-glycosyl group for $R_5$ is preferably a hexose or derivative group thereof. Examples of hexoses include D-glucose, D-fructose, D-mannose, D-galactose and L-galactose. Such derivatives include deoxy sugars (e.g., L- and D-fucose, D-quinovose, L-rhamnose) and amino sugars (e.g., D-glucosamine, D-galactosamine). Deoxy sugars (e.g., L- and D-fucose, D-quinovose, L-rhamnose) are preferred, with greater preference given to L-rhamnose.

Substituents in the amino group for $R_5'$ which may be substituted are exemplified by acyl groups, carbamoyl groups, carbazoyl groups which may be substituted by an acyl group, and amidino groups which may be mono- or di-substituted by an alkyl.

The above-described acyl group and the acyl group in the carbazoyl group which may be substituted by an acyl group are exemplified by nicotinoyl, furoylm and thenoyl.

The alkyl group in the mono- or di-alkylamidino group is a straight-chain or branched alkyl group having 1 to 4 carbon atoms. Such alkyl groups include methyl, ethyl, propyl, isopropyl, butyl, isobutyl, sec-butyl and tert-butyl, with preference given to the methyl group and ethyl group.

Substituents in the amino group for $R_6'$ which may be substituted include alkyl groups, and amidino groups which may be mono- or di-substituted by an alkyl.

The above-described alkyl group and the alkyl group in the mono- or di-alkylamidino group are identical with the alkyl groups defined for $R_5'$ above.

The D-amino acid residue for $R_7$, preferably a D-amino acid residue having 3 to 9 carbon atoms, is exemplified by D-alanyl, D-leucyl, D-valyl, D-isoleucyl and D-phenylalanyl. D-amino acid residues having 3 to 6 carbon atoms, such as D-alanyl and D-valyl, are more preferable.

Still more preferably, $R_7$ is D-alanyl.

The lower alkyl group for Q is identical with the alkyl group defined for $R_5'$ above. Preferably, Q is the methyl group.

$R_1$ is exemplified as follows:

[structures: naphthyl, 4-chlorophenyl]

$R_2$ is exemplified as follows:

[structure: 4-chlorophenyl]

$R_3$ is exemplified as follows:

[structures: (D) pyridylmethyl -NH-CH(CH$_2$-pyridyl)-CO-, (D) benzothienylmethyl -NH-CH(CH$_2$-benzothienyl)-CO-]

$R_4$ is exemplified as follows:

[structures: 4-hydroxyphenyl -OH, 4-(aminoiminomethyl)aminophenyl group with triazole]

$R_5$ is exemplified as follows:

$-(CH_2)_3-NHCO-\text{pyridyl}$, $-(CH_2)_3-NH-CO-NH-NH-CO-\text{furyl}$, $-(CH_2)_3-NH-CO-NH-NH-CO-\text{pyridyl}$, $-(CH_2)_3-NH_2$,  $-(CH_2)_2-NH-CO-NH_2$, $-(CH_2)_3-NH-CO-NH_2$,  $-(CH_2)_3-NH-\overset{NC_2H_5}{\overset{\|}{C}}-NH-C_2H_5$,

[structure: phenyl-NH-C(=N-NH triazole)-NH$_2$]

[structure: sugar ring with OH, CH$_3$, OH, OH]

$R_5$ is exemplified as follows:

$-(CH_2)_3-NH-CH\begin{smallmatrix}CH_3\\CH_3\end{smallmatrix}$, $-(CH_2)_2-NH-\overset{NH}{\overset{\|}{C}}-NH_2$, $-(CH_2)_3-NH-\overset{NC_2H_5}{\overset{\|}{C}}-NH-C_2H_5$ $R_7$ is exemplified as follows:

$\overset{(D)}{-NH-\overset{CH_3}{\underset{|}{CH}}-CO-}$, $\overset{(D)}{-NH-\overset{H}{\underset{|}{N}}-CO-}$ When peptide [II] has one or more kinds of asymmetric carbon atoms, two or more optical isomers are present. Such optical isomers and mixtures thereof are also included in the scope of the present invention.

Peptides represented by general formula [II] can be produced by per se known methods. Example production of such peptides is described in U.S. Pat. No. 5,110,904 and other publications.

Peptide [II] may be used as a salt, preferably a pharmacologically acceptable salt. Such salts include salts formed with inorganic acids (e.g., hydrochloric acid, sulfuric acid, nitric acid), organic acids (e.g., carbonic acid, bicarbonic acid, succinic acid, acetic acid, propionic acid, trifluoroacetic acid) etc., when the peptide has a basic group, such as an amino group. When the peptide has an acidic group, such as a carboxyl group, such salts include salts formed with inorganic bases (e.g., alkali metals such as sodium and potassium, and alkaline earth metals such as calcium and magnesium), organic bases (e.g., organic amines such as triethylamine, and basic amino acids such as arginine) etc. The peptide may form a metal complex compound (e.g., copper complex, zinc complex).

Preferably, the salt of peptide [II] is a salt formed with an organic acid (e.g., carbonic acid, bicarbonic acid, succinic acid, acetic acid, propionic acid, trifluoroacetic acid), with greater preference given to a salt formed with acetic acid.

Examples of particularly preferable peptide [II] and salts thereof are given below.

(1) NAcD2Nal-D4ClPhe-D3Pal-Ser-NMeTyr-DLys(Nic)-Leu-Lys(Nisp)-Pro-DAlaNH$_2$ or its acetate (2) NAcD2Nal-D4ClPhe-D3Pal-Ser-NMeTyr-DLys(AzaglyNic)-Leu-Lys(Nisp)-Pro-DAlaNH$_2$ or its acetate (3) NAcD2Nal-D4ClPhe-D3Pal-Ser-NMeTyr-DLys(AzaglyFur)-Leu-Lys(Nisp)-Pro-DAkaNH$_2$ or its acetate (4)
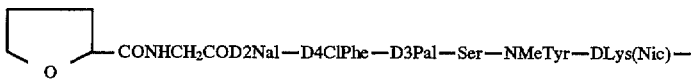
—CONHCH$_2$COD2Nal—D4ClPhe—D3Pal—Ser—NMeTyr—DLys(Nic)—

(5) NAcD2Nal-D4ClPhe-D3Pal-Ser-Tyr-DhArg(Et$_2$)-Leu-hArg(Et$_2$)-Pro-DAlaNH$_2$ or its acetate Abbreviations used in the present specification are defined as follows:

| | |
|---|---|
| NAcD2Nal: | N-acetyl-D-3-(2-naphthyl)alanyl |
| D4ClPhe: | D-3-(4-chlorophenyl)alanyl |
| D3Pal: | D-3-(3-pyridyl)alanyl |
| NMeTyr: | N-methyltyrosyl |
| DLys(Nic): | D-(epsilon-N-nicotinoyl)lysyl |
| Lys(Nisp): | (epsilon-N-isopropyl)lysyl |
| DLys(AzaglyNic): | D-[1-aza-(N-nicotinoyl)glycyl]lysyl |
| DLys(AzaglyFur): | D-[1-aza-(N-2-furoyl)glycyl]lysyl |
| DhArg(Et$_2$): | D-(N,N'-diethyl)homoarginyl |

With respect to the sustained-release preparation of the present invention, the drug content ratio, although varying depending on the kind of the drug, desired pharmacologic effect, duration of effective period and other factors, is preferably about 0.01 to 50% (w/w), more preferably about 0.1 to 40% (w/w), and more preferably about 1 to 30% (w/w), relative to the base ester.

The sustained-release preparation of the present invention, in the form of microcapsules, for instance, can be produced by the following method A or B, or a modification thereof.

(Method A)

First, a drug is dissolved or dispersed in water, with a drug retaining substance, such as gelatin, agar, alginic acid, polyvinyl alcohol or a basic amino acid, dissolved or suspended when necessary, to yield an internal aqueous phase.

The internal aqueous phase may be supplemented with a pH regulator for retaining drug stability or solubility, such as carbonic acid, acetic acid, oxalic acid, citric acid, tartaric acid, succinic acid, phosphoric acid, sodium or potassium salt thereof, hydrochloric acid, sodium hydroxide, arginine, lysine or salt thereof. In addition, albumin, gelatin, citric acid, sodium ethylenediaminetetraacetate, dextrin, sodium hydrogen sulfite, polyol compounds such as polyethylene glycol, etc., as drug stabilizers, and p-oxybenzoates (e.g., methyl paraben, propyl paraben), benzyl alcohol, chlorobutanol, thimerosal etc., as preservatives, may be added.

The internal aqueous phase thus obtained is added to an ester-containing solution (oil phase), followed by emulsification, to yield a W/O emulsion.

The above-described ester-containing solution is prepared by dissolving an ester in an organic solvent. Any organic solvent serves this purpose, as long as it has a boiling point not higher than about 120° C., is sparingly miscible with water and dissolves the ester. Such solvents include halogenated hydrocarbons (e.g., dichloromethane, chloroform, chloroethane, trichloroethane, carbon tetrachloride), fatty acid esters (e.g., butyl acetate), ethers (e.g., isopropyl ether) and aromatic hydrocarbons (e.g., benzene, toluene, xylene). These solvents may be used in combination.

Emulsification is achieved by a conventional dispersing method. Useful dispersing methods include the intermittent shaking method, the method using a mixer, such as a propeller mixer or a turbine mixer, the colloidal mill method, the homogenizer method and the ultrasonication method.

Next, the thus-obtained W/O emulsion is subjected to a microcapsulation process. Useful microcapsulation methods include the in-water drying method, phase separation method and spray drying method described below, and modifications thereof.

(1) In-Water Drying Method

After the W/O emulsion is added to another aqueous phase (third phase) to yield a W/O/W emulsion, the solvent is removed from the oil phase, to yield microcapsules.

An emulsifier may be added to the third, aqueous phase. The emulsifier may be any one, as long as it is capable of forming a stable O/W emulsion. Such emulsifiers include anionic surfactants (e.g., sodium oleate, sodium stearate, sodium lauryl sulfate), nonionic surfactants [e.g., polyoxyethylene sorbitan fatty acid esters (Tween 80, Tween 60, Atlas Powder Company), polyoxyethylene castor oil derivatives (e.g., HCO-60, HCO-50, Nikko Chemicals)], polyvinylpyrrolidone, polyvinyl alcohol, carboxymethyl cellulose, lecithin, gelatin and hyaluronic acid. These emulsifiers may be used singly or in combination. Their concentration can be chosen as appropriate over the range from about 0.001 to 20% (w/w), preferably from about 0.1 to 10% (w/w), and more preferably from about 0.05 to 5% (w/w).

Solvent removal from the oil phase can be achieved by per se known methods, including the method in which the solvent is evaporated under normal or gradually reduced pressure during stirring using a propeller stirrer, magnetic stirrer or the like, and the method in which the solvent is evaporated while the degree of vacuum is adjusted using a rotary evaporator or the like.

The thus-obtained microcapsules are centrifuged or filtered to separate them, after which they are washed with distilled water several times to remove the free drug, drug retaining substance, emulsifier etc. adhering to the microcapsule surface. The microcapsules are then again dispersed in distilled water etc. and lyophilized. To prevent mutual aggregation of particles during washing, an antiaggregation agent may be added to the distilled water for washing. The antiaggregation agent is exemplified by water-soluble polysaccharides such as mannitol, lactol, glucose and starches (e.g., corn starch), amino acids such as glycine and alanine, proteins such as gelatin, fibrin and collagen, and inorganic salts such as sodium chloride, sodium bromide, potassium carbonate and sodium hydrogen phosphate. Where necessary, this is followed by heating under reduced pressure to remove the water and organic solvent from the microcapsules.

(2) Phase Separation Method

For producing microcapsules by the phase separation method, a coacervating agent is gradually added to the above-described W/O emulsion, while the emulsion is stirred, to precipitate and solidify the ester.

Any coacervating agent can be used, as long as it is a polymeric, mineral oil or vegetable oil compound miscible with the solvent for the ester and which does not dissolve the ester. Such coacervating agents include silicon oil, sesame oil, soybean oil, corn oil, cotton seed oil, coconut oil, linseed oil, mineral oil, n-hexane and n-heptane. These may be used in combination of two or more kinds.

The thus-obtained microcapsules are filtered to separate them, after which they are repeatedly washed with heptane etc. to remove the coacervating agent. The free drug and solvent are then removed in the same manner as in the in-water drying method.

(3) Spray Drying Method

The W/O emulsion is sprayed via a nozzle into the drying chamber of a spray drier to volatilize the organic solvent in the fine droplets in a very short time, to yield fine microcapsules. The nozzle is exemplified by the double-fluid nozzle, pressure nozzle and rotary disc nozzle. To prevent microcapsule aggregation where desired, an aqueous solution of the above-described antiaggregation agent may be effectively sprayed via another nozzle, while the organic solvent solution containing the drug and ester is sprayed.

The microcapsules thus obtained may have the water and organic solvent removed at increased temperature under reduced pressure when necessary.

(Method B)

The sustained-release preparation of the present invention can also be produced by dissolving or dispersing a drug and ester in a solvent substantially immiscible with water, and then removing the solvent.

The solvent substantially immiscible with water may be any one, as long as it is substantially immiscible with water, it dissolves the ester and the resulting polymer solution dissolves the drug. Preferably, the solvent has a water solubility not higher than 3% at normal temperature (20° C.), and a boiling point not higher than 120° C. Such solvents include halogenated hydrocarbon (e.g., dichloromethane, chloroform, chloroethane, trichloroethane, carbon tetrachloride), alkyl ethers having 3 or more carbon atoms (e.g., isopropyl ether), fatty acid alkyl (4 or more carbon atoms) esters (e.g., butyl acetate) and aromatic hydrocarbons (e.g., benzene, toluene, xylene). These may be used in combination in appropriate ratios. More preferably, the solvent is a halogenated hydrocarbon (e.g., dichloromethane, chloroform, chloroethane, trichloroethane, carbon tetrachloride), with greater preference given to dichloromethane.

Solvent removal can be achieved by per se known methods, including the method in which the solvent is evaporated under atmospheric or gradually reduced pressure during stirring using a propeller stirrer, magnetic stirrer or the like, and the method in which the solvent is evaporated while the degree of vacuum is adjusted using a rotary evaporator or the like.

The drug is added to the ester solution in the organic solvent to achieve the drug content ratio by weight defined above, to yield an organic solvent solution of the drug and ester. The ester concentration in the organic solvent solution is normally about 0.01 to 80% (w/w), preferably about 0.1 to 70% (w/w), and more preferably about 1 to 60% (w/w), depending on the molecular weight of the ester and the kind of organic solvent. The thus-obtained organic solvent solution of the drug and ester is subjected to a microcapsulation process in the same manner as for the above-described W/O emulsion. Microcapsulation is carried out by, for example, the in-water drying method, phase separation method and spray drying method, or a modification thereof, as described above.

The thus-obtained microcapsules can be administered, as such or in the form of various dosage forms of non-oral preparations (e.g., intramuscular, subcutaneous or visceral injections or indwellable preparations, nasal, rectal or uterine transmucosal preparations) or oral preparations (e.g., capsules such as hard capsules and soft capsules), or solid preparations such as granules and powders or liquid preparations such as syrups, emulsions and suspensions. These preparations can be produced by per se known methods in common use for pharmaceutical production.

An injectable preparation can be prepared by, for example, suspending microcapsules in water, along with a dispersing agent (e.g., Tween 80, HCO-60, carboxymethyl cellulose, sodium alginate), a preservative (e.g., methyl paraben, propyl paraben, benzyl alcohol), an isotonizing agent (e.g., sodium chloride, glycerol, mannitol, sorbitol, glucose) etc., to yield an aqueous suspension, or by dispersing it in a vegetable oil such as olive oil, sesame oil, peanut oil, cotton seed oil or corn oil, propylene glycol, or the like, to yield an oily suspension. A more stable sustained-release injectable preparation can be produced by adding to such an injectable preparation an excipient (e.g., mannitol, sorbitol, lactose, glucose), re-dispersing the microcapsules, then lyophilizing or spray drying the dispersion to solidify it, and adding distilled water for injection or an appropriate dispersant at the time of use.

When microcapsules are used as an injectable suspension, for instance, their particle size is chosen over the range from about 1 to 300 μm, as long as the requirements concerning the degree of dispersion and needle passage are met. Preferably, the particle size is about 5 to 150 μm.

Methods of preparing microcapsules as a sterile preparation include, but are not limited to, the method in which the entire production process is sterile, the method in which gamma rays are used as sterilant, and the method in which an antiseptic is added.

An oral preparation can be produced by, for example, adding an excipient (e.g., lactose, sucrose, starch), a disintegrating agent (e.g., starch, calcium carbonate), a binder (e.g., starch, gum arabic, carboxymethyl cellulose, polyvinylpyrrolidone, hydroxypropyl cellulose) or a lubricant (e.g., talc, magnesium stearate, polyethylene glycol 6000) to microcapsules, subjecting the mixture to compressive shaping, followed by coating to mask the taste or conferring an enteric or sustained-release property when necessary. This coating can be achieved by a per se known method. Useful coating agents include hydroxypropylmethyl cellulose, ethyl cellulose, hydroxymethyl cellulose, hydroxypropyl cellulose, polyoxyethylene glycol, Tween 80, Prullonic F68, cellulose acetate phthalate, hydroxypropylmethyl cellulose phthalate, hydroxypropylmethyl cellulose acetate succinate. Eudragit (Rohm Company, Germany, methacrylic acid-acrylic acid copolymer), and dyes such as titanium oxide and iron oxide red.

The nasal preparation may be solid, semi-solid or liquid. For example, a solid nasal preparation can be produced by powdering the microcapsules, such as or in mixture with an excipient (e.g., glucose, mannitol, starch, microcrystalline cellulose), a thickening agent (e.g., natural rubbers, cellulose derivative, acrylic acid polymer) etc. A liquid nasal preparation can be produced as an oily or aqueous suspension, in almost the same manner as for an injectable preparation. The semi-solid nasal preparation is preferably an aqueous or oily gel or ointment. All these preparations may contain a pH regulator (e.g., carbonic acid, phosphoric acid, citric acid, hydrochloric acid, sodium hydroxide), an antiseptic (e.g., p-oxybenzoate ester, chlorobutanol, benzalkonium chloride) etc.

The suppository may be an oily or aqueous solid, semi-solid or liquid. Any oily base can be used to produce a suppository, as long as it does not dissolve fine particle preparations. Such oily bases include glycerides of higher fatty acids [e.g., cacao fat, uitepsols (produced by Dynamite Nobel Company)], moderate fatty acids [e.g., mygliols (produced by Dynamite Nobel Company)] and vegetable oils (e.g., sesame oil, soybean oil, cottonseed oil). Aqueous bases include polyethylene glycols and propylene glycol. Aqueous gel bases include natural rubbers, cellulose derivatives, vinyl polymers and acrylic acid polymers.

In addition to the above-described microcapsules, the sustained-release preparation of the present invention can be produced by dissolving a biodegradable polymer composition containing a drug dispersed therein by an appropriate method and forming the solution into balls, rods, needles, pellets, films and other forms. The biodegradable polymer composition is produced in accordance with, for example, the method described in Japanese Patent Examined Publication No. 17525/1975. More specifically, the biodegradable polymer composition can be produced by dissolving a drug and a high molecular polymer in a solvent and then removing the solvent by an appropriate method (e.g., spray drying, flush evaporation).

The sustained-release preparation of the present invention can be administered intramuscularly, subcutaneously or intraviscerally as an injectable preparation or implant, intranasally, rectally, or uterinely as transmucosal preparation, or orally [e.g., solid preparations such as a capsule (e.g., hard capsule, soft capsule), granules and powders, and liquid preparations such as syrup, emulsion and suspension]. The sustained-release preparation of the present invention is preferably used as an injectable preparation.

The sustained-release preparation of the present invention has a low toxic potential and can be used safely in mammals (e.g., humans, bovines, swines, dogs, cats, mice, rats, rabbits).

Although varying widely depending on kind, content and dosage form, and duration of release of the drug target disease, subject animal species and other factors, the dose of the sustained-release preparation may be set at any level, as long as the desired effect of the drug is obtained. The dose of the drug per administration can be chosen as appropriate over the range from about 0.01 to 100 mg/kg body weight, preferably from about 0.05 to 50 mg/kg body weight, and more preferably from about 0.1 to 10 mg/kg body weight per adult in the case of a 1-month release preparation.

The dose of the sustained-release preparation per administration can be chosen as appropriate within the range from about 0.1 to 500 mg/kg body weight, preferably from about 0.2 to 300 mg/kg body weight per adult. The frequency of administration can be chosen as appropriate, depending on kind, content and dosage form, duration of release of the drug, target disease, subject animal species and other factors, e.g., once every several weeks, one every month or once every several months.

The present invention is hereinafter described in more detail by means of the following reference examples, examples and experimental examples, which are not to be construed as limitative. In the examples below, % values are by weight, unless otherwise stated.

Reference Example 1

To a 1,000 ml four-necked flask equipped with a nitrogen inlet pipe and a cooling tube, 300 g of a 90% aqueous solution of D,L-lactic acid and 100 g of a 90% aqueous solution of L-lactic acid were charged, followed by heating under reduced pressure in a nitrogen stream from 100° C. and 500 mmHg to 150° C. and 30 mmHg over a 4-hour period to distill off water. After further heating under reduced pressured at 3 to 5 mmHg and 150° to 180° C. for 10 hours, the residue was cooled to yield ambar-colored polylactic acid.

The resulting polymer was dissolved in 1,000 ml of dichloromethane; the solution was added to 60° C. hot water while stirring at constant rate. The separating pasty high molecular polymer was collected and dried at 30° C. under vacuum.

The weight-average molecular and number-average molecular weights by GPC determination and the number-average molecular weight by end-group determination of the polylactic acid thus obtained were determined to be 4,200, 2,192 and 1,572, respectively; the polylactic acid was identified as a polyester having a terminal carboxyl group.

Reference Example 2

To a 1,000 ml four-necked flask equipped with a nitrogen inlet pipe and a cooling tube, 182.5 g of glycolic acid and 166.6 g of D,L-2-hydroxybutyric acid were charged, followed by heating under reduced pressure in a nitrogen stream from 100° C. and 500 mmHg to 150° C. and 30 mmHg over a 3.5-hour period to distill off water. After further heating under reduced pressure at 5 to 7 mmHg and 150° to 180° C. for 32 hours, the residue was cooled to yield an amber-colored glycolic acid-2-hydroxybutyric acid copolymer.

The resulting polymer was dissolved in 1,000 ml of dichloromethane; the solution was added to 60° C. hot water while stirring at constant rate. The separating pasty high molecular polymer was collected and dried at 25° C. under vacuum.

The weight-average molecular weight and number-average molecular weight by GPC determination and number-average molecular weight by end-group determination of the glycolic acid-2-hydroxybutyric acid copolymer thus obtained were determined to be 14,700, 5,700 and 2,400, respectively; the copolymer was identified as a polyester having a terminal carboxyl group.

Example 1

To a mixture of 168 ml of a 40% aqueous solution of potassium hydroxide and 824 ml of ethyl ether, 81.5 g of nitrosomethylurea was added little by little, while the mixture was stirred under ice cooling. The resulting yellow ether layer was separated, and dried with granular potassium hydroxide, followed by removal of potassium hydroxide, to yield about 800 ml of a diazomethane solution.

80 g of polylactic acid having a weight-average molecular weight of about 5,000, produced in the same manner as in Reference Example 1, was dissolved in 500 ml of dichloromethane; this solution was stirred and cooled. While the solution was ice cooled, the above-described diazomethane solution was added dropwise, followed by stirring at room temperature for 2 hours. After the solution was kept standing overnight, the solvent was distilled off under reduced pressure; the residue was vacuum dried at room temperature to yield 79 g of the methyl ester of polylactic acid.

The weight-average and number-average molecular weights by GPC determination and the number-average molecular weight by end-group determination of the polylactic acid methyl ester thus obtained were determined to be 5,250, 2,960 and 1,820, respectively, the residual carboxyl group content as lactic acid, by end-group determination, being under 0.1%; the ester was identified as a polyester having no terminal carboxyl group.

Example 2

To a mixture of 168 ml of a 40% aqueous solution of potassium hydroxide and 1,000 ml of ethyl ether, 104 g of nitrosoethylurea was added little by little, while the mixture was stirred under ice cooling. The resulting yellow ether layer was separated, and dried with granular potassium hydroxide, followed by potassium hydroxide removal, to yield about 900 ml of a diazoethane solution.

130 g of a lactic acid/glycolic acid copolymer having a weight-average molecular weight of about 5,000 (lactic acid/glycolic acid=50/50 (mol %)) was dissolved in 1,900 ml of dichloromethane; this solution was stirred and cooled. While the solution was ice cooled, the above-described diazoethane solution was added dropwise, followed by stirring at room temperature for 2 hours. After the solution was kept standing overnight, the solvent was distilled off under reduced pressure; the residue was vacuum dried at room temperature to yield 131 g of the ethyl ester of lactic acid/glycolic acid.

The weight-average and number-average molecular weights by GPC determination of the lactic acid/glycolic acid ethyl ester thus obtained were determined to be 5,120 and 2,320, respectively, the residual carboxyl group content as lactic acid, by end-group determination, being under 0.1%; the ester was identified as a polyester having no terminal carboxyl group.

Example 3

15 g of a lactic acid/glycolic acid copolymer having a weight-average molecular weight of about 7,500 (lactic acid/glycolic acid=75/25 (mol %)) (Wako Pure Chemical Industries, Ltd.) and a 7.8 g of ethyl iodide were dissolved in 150 ml of acetone. To thus obtained solution was added 1.38 g of potassium carbonate and then the resulting mixture was refluxed for 6 hours. After the resultant solution was cooled, inorganic substances were removed by filtration and then the filtrate was concentrated under reduced pressure. The concentrate was dissolved in 100 ml of dichloromethane, washed 3 times with 100 ml of 10% ethanol-water, and then dried with magnesium sulfate. After magnesium sulfate was separated by filtration, the mixture was concentrated to dryness under reduced pressure to yield 12.5 g of the ethyl ester of lactic acid/glycolic acid copolymer.

The weight-average and number-average molecular weights by GPC determination of the ethyl ester thus obtained were determined to be 5,330 and 3,220 respectively, the residual carboxyl group content as lactic acid, by end-group determination, being under 0.1%; the ester was identified as a polymer having no terminal carboxyl group.

Example 4

9 g of a lactic acid/glycolic acid copolymer having a weight-average molecular weight of about 7,500 (lactic acid/glycolic acid=75/25 (mol %)) (Wako Pure Chemical Industries, Ltd.) was dissolved in a mixed solvent consisting of 20 ml of dichloromethane and 20 ml of ethanol. While thus obtained solution was cooled and stirred, 0.45 ml of triethyl amine, 0.29 ml of ethyl chloroformate and 0.36 g of N,N-dimethylaminopyridine were added. After the resulting mixture was stirred for another 2 hours, 50 ml of dichloromethane and 50 ml of water were added and then dichloromethane phase was separated. The dichloromethane phase was washed 2 times with 50 ml of 10% ethanol-water, and then dried with magnesium sulfate. After magnesium sulfate was separated by filtration, the mixture was concentrated to dryness under reduced pressure to yield 7.7 g of the ethyl ester of lactic acid/glycolic acid copolymer.

The weight-average and number-average molecular weights by GPC determination of the ethyl ester thus obtained were determined to be 9,220 and 5,230 respectively, the residual carboxyl group content as lactic acid, by end-group determination, being under 0.1% the ester was identified as a polymer having no terminal carboxyl group.

Example 5

6 g of a lactic acid/glycolic acid copolymer having a weight-average molecular weight of about 7,500 (lactic acid/glycolic acid=75/25 (mol %)) (Wako Pure Chemical Industries, Ltd.) was dissolved in a mixed solvent consisting of 60 ml of dichloromethane and 60 ml of ethanol. While thus obtained solution was cooled and stirred, 3.83 g of 1-ethyl-3-(3-dimethylaminoisopropyl)-carbodiimide hydrochloride was added and then the reaction mixture was stirred overnight. After 50 ml of water was added, dichloromethane phase was separated. The dichloromethane phase was washed 2 times with 40 ml of 10% ethanol-water and dried with magnesium sulfate. After magnesium sulfate was separated by filtration, the mixture was concentrated to dryness under reduced pressure to yield 5.2 g of the ethyl ester of lactic acid/glycolic acid copolymer.

The weight-average and number-average molecular weights by GPC determination of the ethyl ester thus obtained were determined to be 6,620 and 3,350 respectively, the residual carboxyl group content as lactic acid, by end-group determination, being; under 0.1%; the ester was identified as a polymer having no terminal carboxyl group.

Example 6

4.4 g of a 1:1 mixture of the glycolic acid/2-hydroxybutyric acid copolymer obtained in Reference Example 2 and the polylactic acid methyl ester obtained in Example 1 was dissolved in 9.1 g (7.0 ml) of dichloromethane. In this solution was dissolved 600 mg of the acetate of NAcD2Nal-D4ClPhe-D3Pal-Ser-NMeTyr-DLys(Nic)-Leu-Lys(Nisp)-Pro-DAlaNH$_2$ (produced by TAP Company, hereinafter referred to as biologically active peptide A), produced by the method described in U.S. Pat. No. 5,110,904. The resulting solution was poured into 1,000 ml of a 0.1% aqueous solution of polyvinyl alcohol (EG-40, produced by The Nippon Synthetic Chemical Industry Co., Ltd.), previously adjusted to 17° C., and was the prepared as an O/W emulsion using a turbine type homomixer at 7,000 rpm. This O/W emulsion was stirred at room temperature for 3 hours to volatilize off the dichloromethane and solidify the oil phase, which was then collected via centrifugation at 1,500 rpm using a centrifuge (O5PR-22, Hitachi Limited). The oil phase as again dispersed in distilled water, followed by centrifugation to wash off the free drug etc. After the collected microcapsules were again dispersed in a small amount of distilled water, 0.3 g of D-mannitol was added; the resulting dispersion was lyophilized to yield a powder. The biologically active peptide A content of the microcapsules was 9.3%.

Example 7

1.0 g of a 1:1 mixture of a lactic acid/glycolic acid copolymer having a weight-average molecular weight of 5,100 (lactic acid/glycolic acid=50/50 (mol %)) (Wako Pure Chemical Industries, Ltd.) and the lactic acid/glycolic acid ethyl ester obtained in Example 2 was dissolved in 2.0 g (1.5 ml) of dichloromethane. In this solution, 40 mg of human interferon alpha ($7.0 \times 10^7$ IU/ml) was dispersed. The resulting dispersion was poured into 300 ml of a 0.1% aqueous solution of polyvinyl alcohol (EG-40, produced by The Nippon Synthetic Chemical Industry Co., Ltd.), previously adjusted to 17° C., and was then prepared as an O/W emulsion using a turbine type homomixer at 6,500 rpm. This O/W emulsion was stirred at room temperature for 3 hours to volatilize off the dichloromethane and solidify the oil phase, which was then collected via centrifugation using a centrifuge (O5PR-22, Hitachi Limited) at 1,500 rpm. The oil phase was again dispersed in distilled water, followed by centrifugation to wash off the free drug etc. After the collected microcapsules were again dispersed in a small amount of distilled water, 50 mg of D-mannitol was added; the resulting dispersion was lyophilized to yield a powder. The human interferon alpha activity of the microcapsules was $5.75 \times 10^5$ IU/mg microcapsule.

Example 8

1.0 g of the lactic acid/glycolic acid ethyl ester obtained in Example 2 was dissolved in 2.0 g (1.5 ml) of dichloromethane. In this solution, 40 mg of human interferon alpha ($2.0 \times 10^8$ IU/mg) was dispersed. The resulting dispersion was poured into 300 ml of a 0.1% aqueous solution of polyvinyl alcohol (EG-40, produced by The Nippon Synthetic Chemical Industry Co., Ltd.), previously adjusted to 17° C., and was then prepared as an O/W emulsion, using a turbine type homomixer at 6,500 rpm. This O/W emulsion was stirred at room temperature for 3 hours to volatilize off the dichloromethane and solidify the oil phase, which was then collected via centrifugation at 1,500 rpm using a centrifuge (O5PR-22, Hitachi Limited). The oil phase was again dispersed in distilled water, followed by centrifugation to wash off the free drug etc. After the collected microcapsules were again dispersed in a small amount of distilled water, 50 mg of D-mannitol was added; the resulting dispersion was lyophilized to yield a powder. The human interferon alpha activity of the microcapsules was $2.48 \times 10^5$ IU/mg microcapsule.

Example 9

0.9 g of a 1:1 mixture of a lactic acid/glycolic acid copolymer having a weight-average molecular weight of 5,100 (lactic acid/glycolic acid=50/50 (mol %)) (Wako Pure Chemical Industries, Ltd.) and the lactic acid/glycolic acid ethyl ester obtained in Example 2 was dissolved in 2.0 g (1.5 ml) of dichloromethane. In this solution, 100 mg of recombinant insulin (Wako Pure Chemical Industries, Ltd.) was dispersed. The resulting dispersion was poured into 350 ml of a 0.1% aqueous solution of polyvinyl alcohol (EG-40, produced by The Nippon Synthetic Chemical Industry Co., Ltd.) containing 5% mannitol, previously adjusted to 18° C., and was then prepared as an O/W emulsion using a turbine type homomixer at 6,500 rpm. This O/W emulsion was stirred at room temperature for 3 hours to volatilize off the dichloromethane and solidify the oil phase, which was then collected via centrifugation using a centrifuge (O5PR-22, Hitachi Limited) at 1,500 rpm. The oil phase was again dispersed in distilled water, followed by centrifugation to wash off the free drug etc. After the collected microcapsules were again dispersed in a small amount of distilled water, 50 mg of D-mannitol was added; the resulting dispersion was lyophilized to yield a power (476 mg). The insulin content of the microcapsules was 7.95%.

Example 10

4.5 g of a 1:1 mixture of the lactic acid/glycolic acid copolymer having a weight-average molecular weight of 5,000 (lactic acid/glycolic acid=50/50 (mol %)) (Wako Pure Chemical Industries, Ltd.), and the lactic acid/glycolic acid ethyl ester obtained in Example 2 was dissolved in 6.5 g (5.0 ml) of dichloromethane. To this solution was added 500 mg of the acetate of N-(s)-Tetrahydrofur-2-oyl-Gly-D2Nal-D4ClPhe-D3Pal-Ser-NMeTyr-DLys(Nic)-Leu-Lys(Nisp)-Pro-DAlaNH$_2$ (produced by TAP Company, hereinafter referred to as biologically active peptide B) dissolved in 0.6 ml of distilled water, followed by mixing for 60 seconds with a turbine type homomixer to yield a W/O emulsion. This W/O was cooled to 16° C., poured into 1,000 ml of a 0.1% aqueous solution of polyvinyl alcohol (EG-40, produced by The Nippon Synthetic Chemical Industry Col, Ltd.), previously adjusted to 16° C., and was then prepared as a W/O/W emulsion using a turbine type homomixer at 7,000 rpm. This W/O/W emulsion was stirred at room temperature for 3 hours to volatilize off the dichloromethane and solidify the W/O emulsion, which was then collected via centrifugation at 2,000 rpm using a centrifuge (O5PR-22, Hitachi Limited). And then, microcapsules were obtained as a powder in the same manner as Example 6. The biologically active peptide B content of the microcapsules was 9.2%.

Comparative Example 1

1.5 g of the lactic acid/glycolic acid copolymer having a weight-average molecular weight of 5,100 (lactic acid/glycolic acid=50/50 (mol %)) (Wako Pure Chemical Industries, Ltd.) was dissolved in 2.6 (2.0 ml) of dichloromethane. In this solution, 60 mg of human interferon alpha ($1.5 \times 10^8$ IU/mg) was dispersed. The resulting dispersion was poured into 300 ml of a 0.1% aqueous solution of polyvinyl alcohol (EG-40, produced by The Nippon Synthetic Chemical Industry Co., Ltd.), previously adjusted to 17° C., and was then prepared as an O/W emulsion, using a turbine type homomixer at 6,500 rpm. This O/W emulsion was stirred at room temperature for 3 hours to volatilize off the dichloromethane and solidify the oil phase, which was then collected via centrifugation at 1,500 rpm using a centrifuge (O5PR-22, Hitachi Limited). The oil phase was again dispersed in distilled water, followed by centrifugation to wash off the free drug etc. After the collected microcapsules were again dispersed in a small amount of distilled water, 50 mg of D-mannitol was added, the resulting dispersion was lyphilized to yield a powder. The human interferon alpha activity of the microcapsules was $2.24 \times 10^6$ IU/mg microcapsule.

Experimental Example 1

About 14 mg of the microcapsules obtained in Example 6 (1.35 mg of biologically active peptide A contained) was dispersed in 0.5 ml of a dispersant (a solution of 2.5 mg of carboxymethyl cellulose, 0.5 mg of Polysorbate 80 and 25 mg of mannitol in distilled water). This dispersion was subcutaneously administered via 22-gauge injection needle to the backs of male SD rats at 10 weeks of age. Following administration, blood was regularly taken from each rat via the tail vein, and assayed for biologically active peptide A content by RIA. The results are given in Table 1.

TABLE 1

| | biologically active Peptide A Concentration (ng/ml) | | | | | |
|---|---|---|---|---|---|---|
| | Day 1 | Week 1 | Week 2 | Week 3 | Week 4 | Week 6 |
| Experimental Example 1 | 1.75 | 4.41 | 4.31 | 3.19 | 2.43 | 0.76 |

When polylactic acid having a methyl-esterified terminal carboxyl group was used, low blood drug levels were obtained 1 day after administration, demonstrating very low initial drug release after administration. The blood drug level remained almost constant over a 1-month period, indicating a good sustained-release property.

Experimental Example 2

About 87 mg of the microcapsules obtained in Example 7 ($5.0 \times 10^7$ IU human interferon alpha contained) was dispersed in 0.5 ml of a dispersant (a solution of 2.5 mg of carboxymethyl cellulose, 0.5 mg of Polysorbate 80 and 25 mg of mannitol in distilled water). This dispersion was subcutaneously administered via 22-gauge injection needle to the backs of male SD rats at 8 weeks of age. Following administration, blood was regularly taken from each rat via the tail vein, and assayed for human interferon alpha content by EIA. The results were given in Table 2.

Experimental Example 3

The microcapsules obtained in Comparative Example 1 were treated in the same manner as in Experimental Example 2 to determine the blood human interferon alpha content. The results are given in Table 2.

TABLE 2

| | Human Interferon Alpha Concentration (IU/ml) | | | | | | |
|---|---|---|---|---|---|---|---|
| | 3 Hours | 6 Hours | Day 1 | Day 2 | Day 3 | Day 7 | Day 9 |
| Experimental Example 2 | 5042.6 | 3934.3 | 162.3 | 122.6 | 139.9 | 113.8 | 43.8 |
| Experimental Example 3 | 5127.2 | 6121.6 | 65.9 | 42.9 | 32.3 | 1.9 | 0.0 |

When a lactic acid/glycolic acid copolymer having an ethylated terminal carboxyl group was used, initial drug release was suppressed, while a high stationary blood drug level was maintained, demonstrating a good sustained-release property.

Experimental Example 4

About 20 mg of the microcapsules obtained in Example 8 ($5.0 \times 10^7$ IU human interferon alpha contained) was dispersed in 0.5 ml of a dispersant (a solution of 2.5 mg of carboxymethyl cellulose, 0.5 mg of Polysorbate 80 and 25 mg of mannitol in distilled water). This dispersion was subcutaneously administered via 22-gauge injection needle to the backs of male SD rats at 8 weeks of age. Following administration, blood was regularly taken from each rat via the tail vein, and assayed for human interferon alpha content by EIA.

Despite the fact that the dose per rat was almost the same as in Experimental Example 2, the blood human interferon alpha concentration remained as high as 133 IU/ml even at day 14 following administration. Good sustained-release was obtained when a lactic acid/glycolic acid copolymer having an ethylated terminal carboxyl group was used.

The ester of the present invention, can be used as a matrix for sustained-release preparation. The matrix is stable to light, heat, moisture, coloring, etc., and is of low toxicity.

The sustained-release preparation produced by using the ester of the present invention offers stable drug release over an extended period of time, ensuring sustained stable effect. Furthermore, the sustained-release preparation does not show excess drug release just after administration.

What is claimed is:

1. A matrix for sustained-release preparation comprising an ester formed at a terminal carboxyl group of a straight-chain polyester which essentially consists of an α-hydroxymonocarboxylic acid, the polyester having a weight-average molecular weight of about 1,500 to about 50,000.

2. The matrix according to claim 1, wherein the straight-chain polyester is a lactic acid/glycolic acid copolymer.

3. The matrix according to claim 1, wherein the ester is an alkyl ester.

4. The matrix according to claim 3, wherein the alkyl ester is a $C_{1-3}$ alkyl ester.

5. A sustained-release preparation which comprises the matrix as claimed in claim 1 an a biologically active peptide.

6. The sustained-release preparation according to claim 5, wherein the biologically active peptide is an LH-RH analogue.

7. The sustained-release preparation according to claim 6, wherein the LH-RH analogue is an LH-RH antagonist.

8. The sustained-release preparation according to claim 5, wherein the biologically active peptide is a cytokine.

9. The sustained-release preparation according to claim 8, wherein the cytokine is an interferon.

10. An injectable preparation which comprises the sustained-release preparation as claimed in claim 5.

* * * * *